(12) United States Patent
Humphrey et al.

(10) Patent No.: US 10,184,882 B2
(45) Date of Patent: Jan. 22, 2019

(54) SYSTEM AND METHOD FOR PROVIDING USER GUIDANCE FOR ELECTRONIC DEVICE PROCESSING

(71) Applicant: ATC Logistics & Electronics, Inc., Fort Worth, TX (US)

(72) Inventors: Clark Humphrey, Fort Worth, TX (US); Joel McCarty, Fort Worth, TX (US); Brian Morris, Fort Worth, TX (US)

(73) Assignee: FEDEX SUPPLY CHAIN LOGISTICS & ELECTRONCIS, INC., Fort Worth, TX (US)

( * ) Notice: Subject to any disclaimer, the term of this patent is extended or adjusted under 35 U.S.C. 154(b) by 1060 days.

(21) Appl. No.: 14/203,110

(22) Filed: Mar. 10, 2014

(65) Prior Publication Data

US 2014/0278244 A1 Sep. 18, 2014

Related U.S. Application Data

(60) Provisional application No. 61/777,924, filed on Mar. 12, 2013.

(51) Int. Cl.
| | | |
|---|---|---|
| G06F 11/00 | (2006.01) | |
| G01N 21/01 | (2006.01) | |
| G06F 11/22 | (2006.01) | |

(52) U.S. Cl.
CPC ............ G01N 21/01 (2013.01); G06F 11/22 (2013.01)

(58) Field of Classification Search
CPC ................................ G06F 11/00; G01N 21/01

USPC ......................................................... 702/182
See application file for complete search history.

(56) References Cited

U.S. PATENT DOCUMENTS

| | | | | |
|---|---|---|---|---|
| 5,666,493 A | * | 9/1997 | Wojcik ................. | G06Q 10/087 705/22 |
| 8,429,409 B1 | * | 4/2013 | Wall ...................... | H04W 12/04 713/172 |
| 2002/0010784 A1 | * | 1/2002 | Clayton .............. | G06F 21/6245 709/229 |
| 2002/0040325 A1 | * | 4/2002 | Takae ................... | G06Q 10/087 705/302 |
| 2003/0103451 A1 | * | 6/2003 | Lutgen .................... | H04L 47/10 370/229 |
| 2003/0182504 A1 | * | 9/2003 | Nielsen ................ | G06F 3/0601 711/114 |
| 2005/0154919 A1 | * | 7/2005 | Noguchi ................. | G06F 21/32 726/4 |
| 2005/0266885 A1 | * | 12/2005 | Katayanagi ......... | H04L 63/0853 455/558 |
| 2006/0025177 A1 | * | 2/2006 | Tu ........................... | H04M 1/66 455/558 |

(Continued)

Primary Examiner — Oluseye Iwarere
(74) Attorney, Agent, or Firm — McGuireWoods LLP

(57) ABSTRACT

A system and method for processing an electronic device. The electronic device is identified. User instructions associated with the electronic device are retrieved utilizing a testing system. The user instructions are communicated from the testing system for performing cosmetic inspection of the electronic device, customer personal information (CPI) analysis of the electronic device, software analysis of the electronic device, validation and restoring of default content software and settings, and functional testing. Verification information is received from a user of implementation of the user instructions.

13 Claims, 5 Drawing Sheets

(56) References Cited

U.S. PATENT DOCUMENTS

| | | | |
|---|---|---|---|
| 2007/0082705 A1* | 4/2007 | Jain | H04M 1/66 455/558 |
| 2009/0075630 A1* | 3/2009 | McLean | G06F 21/602 455/411 |
| 2009/0279507 A1* | 11/2009 | Kanazawa | H04W 36/24 370/332 |
| 2009/0312055 A1* | 12/2009 | Liu | H04B 1/3805 455/558 |
| 2010/0088192 A1* | 4/2010 | Bowles | G06Q 10/30 705/26.1 |
| 2010/0161397 A1* | 6/2010 | Gauthier | G01C 21/3605 705/14.4 |
| 2010/0169231 A1* | 7/2010 | Bowles | G06Q 10/30 705/306 |
| 2011/0030067 A1* | 2/2011 | Wilson | G06F 21/6245 726/27 |
| 2012/0079100 A1* | 3/2012 | McIntyre | G06F 11/0742 709/224 |
| 2012/0116929 A1* | 5/2012 | Gventer | G06F 21/6245 705/28 |
| 2012/0117001 A1* | 5/2012 | Gventer | G06F 17/30073 705/500 |
| 2012/0191562 A1* | 7/2012 | Bowles | G06Q 10/00 705/26.3 |
| 2012/0198279 A1* | 8/2012 | Schroeder | G06F 11/2294 714/32 |
| 2013/0046611 A1* | 2/2013 | Bowles | G06Q 10/00 705/14.37 |
| 2013/0046699 A1* | 2/2013 | Bowles | G06Q 10/00 705/306 |
| 2013/0124426 A1* | 5/2013 | Bowles | G06Q 99/00 705/308 |
| 2013/0144797 A1* | 6/2013 | Bowles | G06Q 30/0278 705/306 |
| 2013/0191236 A1* | 7/2013 | Bowles | G06Q 10/30 705/26.3 |
| 2013/0198089 A1* | 8/2013 | Bowles | G06Q 10/30 705/308 |
| 2013/0198144 A1* | 8/2013 | Bowles | G06Q 10/30 707/668 |
| 2013/0311318 A1* | 11/2013 | Librizzi | G06Q 10/00 705/26.3 |
| 2014/0026226 A1* | 1/2014 | Aoki | G06F 21/6245 726/26 |
| 2014/0059696 A1* | 2/2014 | Gventer | G06F 17/30073 726/26 |
| 2014/0059697 A1* | 2/2014 | Gventer | G06F 17/30073 726/26 |
| 2014/0156883 A1* | 6/2014 | Bowles | G06F 13/10 710/33 |
| 2016/0098690 A1* | 4/2016 | Silva | G06Q 10/30 705/21 |
| 2016/0253274 A1* | 9/2016 | Huang | G06F 13/102 710/33 |
| 2018/0032952 A1* | 2/2018 | Wada | G01D 4/006 |

* cited by examiner

*FIG. 4*

| Graphical User Interface | 400 |

| ☑ | Testing Initiated | Username | JMc |
| | | Password | ******** |
| ☐ | Testing Finished | Customer/Company ID | 3415 |

Testing Information

☐ Device Identifier/IMEI _____
☐ File/Memory Location: _____
☐ File Type: _____
☐ Device received from: _____
☐ Date CPI cleared: _____
☐ Individual performing CPI removal: _____
☐ CPI removal reported with the receipt of the report received? Date: _____
☐ Individual performing CPI removal: _____

Device Functional

☑ Start-up Verified
☑ Functionality Verified
☑ Operating System Restored
☑ Co-branding Restored: Graphics, ringtone, theme
☑ Settings: Radio on, language options, security certificates
☑ Included memory devices cleared
☑ Applications installed: _____
☑ Issues: Chipped screen, images removed

SYSTEM AND METHOD FOR PROVIDING USER GUIDANCE FOR ELECTRONIC DEVICE PROCESSING

RELATED PATENT APPLICATIONS

This application claims priority to Provisional Patent application 61/777,924 filed Mar. 12, 2013 entitled "SYSTEM AND METHOD FOR PROVIDING USER GUIDANCE FOR ELECTRONIC DEVICE PROCESSING" and Provisional Patent Application 61/777,943 filed Mar. 12, 2013 which is hereby incorporated by reference in its entirety. This application is a related to U.S. patent application Ser. No. 12/940,331 filed Nov. 5, 2010 entitled "SYSTEM AND METHOD FOR REMOVING CUSTOMER PERSONAL INFORMATION FROM AN ELECTRONIC DEVICE", which is a co-pending application of U.S. patent application Ser. No. 12/940,411 entitled "SYSTEM AND METHOD FOR FLASHING A WIRELESS DEVICE" filed on Nov. 5, 2010; Ser. No. 12/940,346 entitled "SYSTEM AND METHOD FOR AUDITING REMOVAL OF CUSTOMER PERSONAL INFORMATION ON ELECTRONIC DEVICES" filed on Nov. 5, 2010; Ser. No. 12/940,299, entitled "SYSTEM AND METHOD FOR TRACKING CUSTOMER PERSONAL INFORMATION IN A WAREHOUSE MANAGEMENT SYSTEM" filed on Nov. 5, 2010; and U.S. patent application Ser. No. 13/434,507 entitled "SYSTEM AND METHOD FOR RECEIVING QUALITY ISSUE LOG." The teachings and disclosures of which are each hereby incorporated in their entireties by reference thereto.

BACKGROUND

The use of and development of communications has grown nearly exponentially in recent years. The growth is fueled by larger networks, more reliable protocols, enhanced software functionality, and better communications hardware available to service providers and consumers. As a result, more people than ever are buying and using electronic devices. Correspondingly, the number of returns, repairs, and refurbishments are at record levels creating logistical problems.

Under various circumstances, users may return electronic devices to an original equipment manufacturer (OEM), retailer, repair facility, service provider, or other entity. Electronic devices are often returned for repairs, refurbishment, exchanges, warranty issues, or any number of other justified or arbitrary reasons. It is imperative that any electronic device that has been returned be cosmetically inspected, tested for functionality, and cleared of all personal information, sensitive data, or other information linked to a previous user. For example, if the personal information is not removed, applicable laws, industry standards, and common business practices may be violated. For example, the personal information may be used by another party to perpetrate an act of identity theft. Similarly, the privacy of a previous user may be otherwise violated. In addition, if devices are not cosmetically and functionally tested, electronic devices may be incorrectly redistributed, recycled, or otherwise processed.

SUMMARY

One embodiment includes a system and method for processing an electronic device. The electronic device may be identified. User instructions associated with the electronic device may be retrieved utilizing a testing system. The user instructions may be communicated from the testing system for performing cosmetic inspection of the electronic device, customer personal information (CPI) analysis of the electronic device, software analysis of the electronic device, and functional testing. Verification information may be received from a user of implementation of the user instructions.

Another embodiment includes a system for performing processing of an electronic device. The system may include an imaging system configured to analyze the electronic device and information presented by one or more displays of the electronic device. The system may also include a number of robotic arms configured to secure the electronic device and provide input to the selection components of the electronic device. The system may also include a database configured to store instructions for processing the electronic device and test results from performing the processing. The system may also include a controller configured to identifying the electronic device utilizing the imaging system, retrieve the instructions associated with the electronic device, perform a cosmetic inspection utilizing the imaging system, analyze software of the electronic device, and determine whether CPI is present on the electronic device.

Yet another embodiment provides a testing system. The testing system may include a processor for executing a set of instructions and a memory for storing the set of instructions. The set of instructions may be executed to identify an electronic device, retrieve user instructions associated with the electronic device utilizing a testing system, present the user instructions for performing cosmetic inspection of the electronic device, customer personal information (CPI) analysis of the electronic device, software analysis of the electronic device, and functional verification, and receive verification information from a user of one or more of the user instructions.

BRIEF DESCRIPTION OF THE DRAWINGS

Illustrative embodiments of the present invention are described in detail below with reference to the attached drawing figures, which are incorporated by reference herein and wherein:

FIG. 4 is a pictorial representation of a graphical user interface 400 for testing an electronic device in accordance with an illustrative embodiment.

DETAILED DESCRIPTION OF THE DRAWINGS

The illustrative embodiments provide a system, method, and devices for processing electronic devices. In one embodiment, the system includes a testing system including a computing device configured to display information and instructions to a user or operator for processing electronic devices. The testing system may prompt the user to perform a visual or cosmetic inspection of the electronic device, remove customer personal information (CPI), remove software, and document the results of the processing for verification and reporting. The user may perform various steps to process the electronic device for further distribution, such as recycling, repair, cleaning, refurbishment and redistribution. The testing system may provide specific instructions and require user answers or verifications to move between each step.

As a result, accountability may be taken by the user and system for each of the important steps that may be performed. The testing steps and the results may be tested, recorded, and associated with the electronic device utilizing one or more identifiers. For example, identifiers may include serial numbers, model numbers, stock keeping unit (SKUs), bar codes, quick response (QR) codes, radio frequency identification tags, customized identification stickers, labels, MAC addresses, IP addresses, IMEIs, or other physical or electronic identifiers entered by the user, scanned from the electronic device (automatically or manually), or otherwise determined.

In another embodiment, the testing system may automatically process the electronic device. For example, the electronic device may be connected to the testing system electronically through a wired connection or wireless connections. The electronic device may be connected by a user or automatically by the robotic testing system. The testing system may include one or more arms, plungers, grippers, or input devices for activating the physical buttons of the electronic device (e.g. power button, volume, menu, etc.) and the soft buttons (e.g. touch screen selection components, icons, soft keys, etc.) of the electronic device. Any of the described steps may be performed by the automated testing system. In one embodiment, an imaging system may be utilized to analyze the electronic device and perform the processing systems based on the viewed results.

Figure 1:
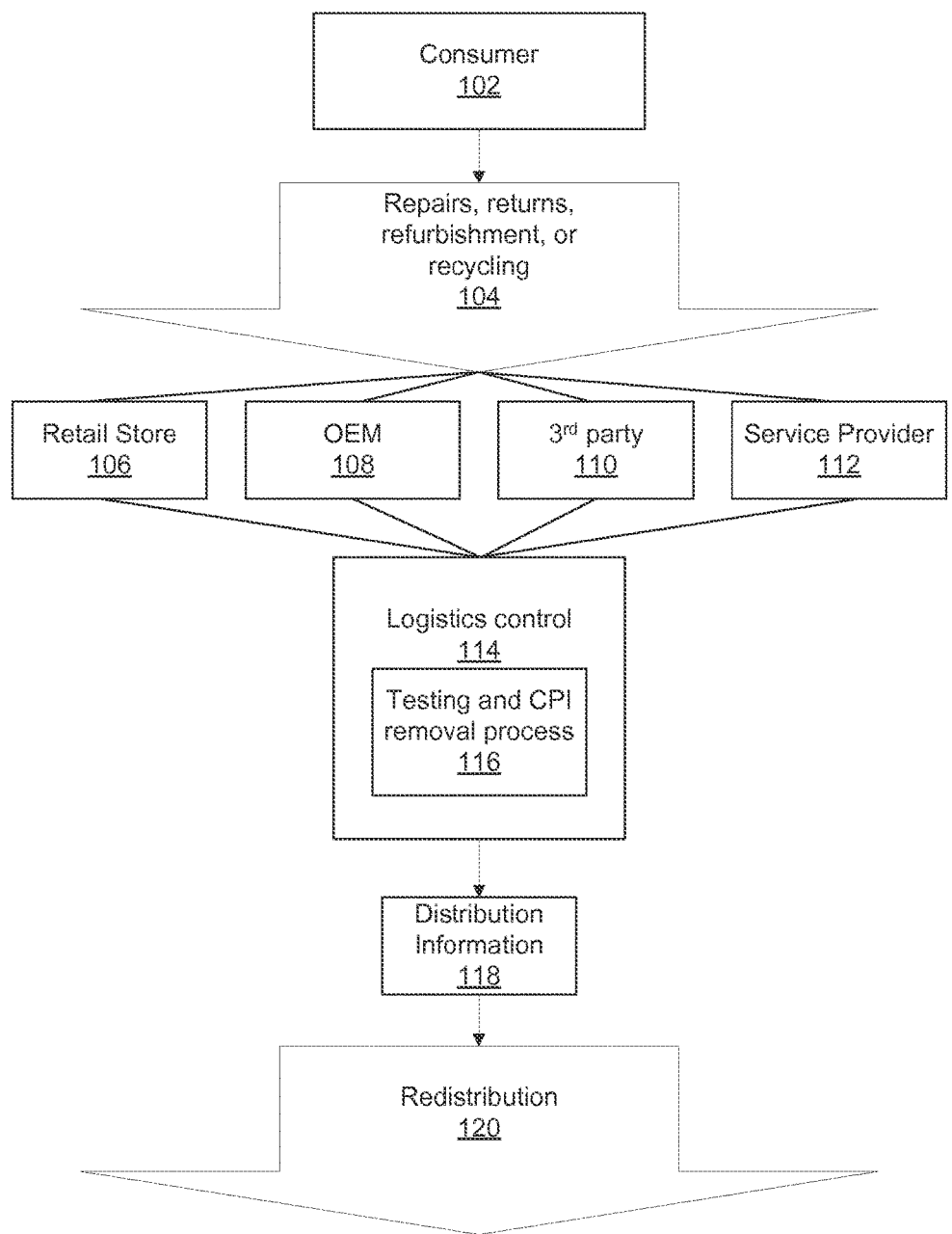
FIG. 1 is a flow diagram of a process flow for processing electronic devices in accordance with an illustrative embodiment.

FIG. 1 is a flow diagram of a process flow 100 for processing electronic devices in accordance with an illustrative embodiment. The process flow 100 illustrates one embodiment of electronic devices being managed and processed for subsequent redistribution. The process flow 100 may include any number of users, participants, steps, and systems that may be automated or implemented based on user input, commands, instructions, feedback, and interaction.

In one embodiment, a consumer 102 returns one or more electronic devices. The consumer 102 may physically present the electronic device, ship the device, or connect the device to a portal or an interface managed by a service provider. In certain embodiments, the consumer 102 may access one or more websites, cloud based applications, or use a downloadable application to facilitate the return or shipping of an electronic device for one or more of the disclosed purposes. For instance, in one embodiment, the electronic device is presented or supplied for repairs, returns, order fulfillment, refurbishment, or recycling 104. In addition, the electronic device may be received for any number of other purposes not specifically described such as, but not limited to, upgrades, reconfiguration, clearing of personal data, reloading operating system software, restoring default content and settings, or user transfer. The consumer 102 may represent an individual user, group, organization, business, service provider, or other party.

In one embodiment, the parties that may communicate or interact with the consumer 102 to receive the electronic device(s) for repairs, returns, order fulfillment, refurbishment, or recycling 104 may include a retail store 106, an OEM 108, a third party 110 and a service provider 112 (collectively, the "parties" 113). As previously described, the retail store 106, OEM 108, third party 110 and service provider 112 represent a few of many possible parties, organizations, groups or individuals that may receive the electronic devices. The parties 113 may physically or electronically present electronic devices to a logistics control 114.

In one embodiment, the logistics control 114 is a warehouse management facility, system, or operation that is operable to process electronic devices for repairs, returns, refurbishment or recycling 104. The warehouse management system may also represent one or more of a receiving system, a shipping system, a tracking system, a CPI removal system, and a returns system. The logistics control 114 may have legal or contractual obligations or agreements with the parties 113 to process the electronic devices. The logistics control 114 may also be utilized when the parties 113 need to process an electronic device in a way which is incompatible with their business model, technical skills, or day-to-day operations.

The logistics control 114 may include any number of systems, equipment, and devices configured to test one or more electronic devices. In one embodiment, the logistics control 114 may implement a testing and CPI removal process 116 in order to test the electronic devices and clear the CPI from electronic devices for subsequent reuse and/or redistribution. For example, a number of users may connect electronic devices to a test stand to detect and remove CPI for a service provider. The users may be provided instructions for step-by-step verifiably removing the CPI even if they are not trained or have knowledge of each specific electronic device. The testing and CPI removal process 116 implemented by the logistics control 114 is further described in terms of systems, devices, interfaces, and methods described herein.

In certain embodiments, the testing and CPI removal process 116 also includes a quality control (QC) inspection procedure to ensure that default content software and settings are intact so that an electronic device functions correctly and provides the appropriate "out of the box" experience for the next recipient of the device.

The testing and CPI removal process 116 may track and record all information relevant to the removal of CPI information and the validation of default content software and settings from the electronic devices for subsequent access or reporting performed by the logistics control 114 or the parties 113. In one embodiment, the testing and CPI removal process 116 includes a portal and database storing the CPI-related information for retrieval by the logistics control 114 and the parties 113. The logistics control 114 may include any number of different facilities or systems that may operate independently or may be networked. As a result, the testing and CPI removal process 116 may communicate with any number of other logistical control centers and testing and CPI removal systems and processes to perform user prompting, tracking, reporting, auditing, and verification.

If, or once, electronic devices are satisfactorily cleared of all CPI and/or default content software and settings are restored, distribution information may be utilized as part of redistribution 120. Redistribution 120 may include returning the individual electronic devices to the respective parties 113 or the consumer 102, sending the electronic devices according to the distribution information 118, selling the electronic devices to users, businesses, or other entities, or otherwise shipping or processing the electronic devices.

In one embodiment, in which the testing and CPI removal process 116 is performed remotely from the facility or systems of the consumer 102 or the parties 113, redistribution 120 may entail returning control to the applicable parties or activating or authorizing the electronic devices to function normally. For example, once the logistics control 114 begins implementing management of the electronic devices, all other functionality may be locked out for the electronic devices (with the exception of failsafe or failover operations). In another example, a user may access a server through a website to be walked through steps for updating software, deleting CPI, and otherwise processing the electronic device as is herein described.

Figure 2:
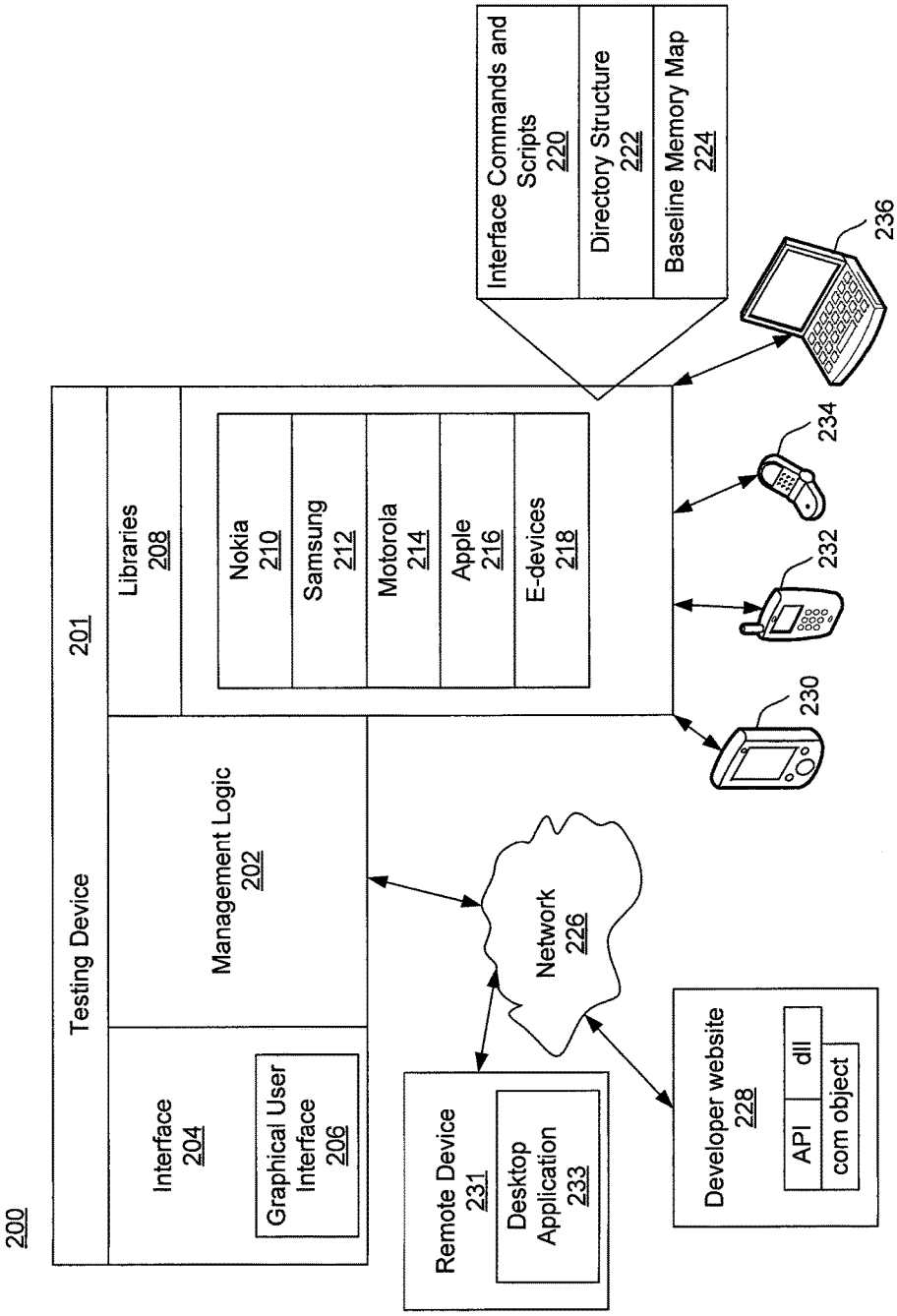
FIG. 2 is a block diagram of a testing system for testing electronic devices in accordance with an illustrative embodiment.

FIG. 2 is a block diagram of a testing system 200 for removing customer private information in accordance with an illustrative embodiment. The testing system 200 is one embodiment of a device, networked computing system, or environment in which a number of tests may be performed including cosmetic inspection, start-up and functionality verification, CPI detection, removal, auditing, and reporting, software updating, validation of default content software and settings, and other requested or required tests for a number of electronic devices. One or more users or operators (not shown) may interact with different portions of the testing system 200 simultaneously or concurrently.

In one embodiment, the testing system 200 may include a testing device 201 or system. The testing device 201 may be utilized to perform the tests. In one embodiment, the testing device 201 may include management logic 202, an interface 204, a graphical user interface 206, libraries and models 208 including, but not limited to, libraries for Nokia 210, Samsung 212, Motorola 214, Apple 216, E-devices 218, interface commands and scripts 220, a directory structure 222 and a baseline memory map 224. The testing device 201 may further communicate with a network 226. The network 226 may communicate with a developer website 228. The testing system 200 may be utilized to test electronic devices 230-236.

In one embodiment, the testing device 201 is a personal computing device, such as a desktop computer configured to communicate with one or more electronic devices 230-236 concurrently or simultaneously. In another embodiment, the testing device 201 may be a server, tablet, wireless device, visual glasses system, or other network device that acts as a master WMS, receiving system, auditing system, return system, tracking system, or shipping system that is accessible to any number of remote computing devices or terminals to perform the methods herein described.

The testing device 201 may include any number of computing or communications components not specifically described herein including, but not limited to, motherboards, busses, ports, cards, interfaces, adapters, peripherals, displays, jacks, processors, memories, operating systems, applications, modules, displays, or similar hardware or software components. The testing device 201 may include WMS hardware, software, equipment, and interfaces in addition to the described components.

In one embodiment, the management logic 202 is the logic that prompts the user to perform testing or automatically implements identification and testing. The management logic 202 may include one or more processors and memories configured to execute commands, instructions, or codes to perform the testing management. For example, the management logic 202 may be hardware configured to perform the method herein described and updated as needed. In another embodiment, the management logic 202 may be a core software executive or a software module that controls the other functions of the testing device 201.

The processor of the management logic 202 is circuitry or logic enabled to control execution of a set of instructions. The processor may be microprocessors, digital signal processors, application-specific integrated circuits (ASIC), field programmable gate array (FPGA) central processing units, or other devices suitable for controlling an electronic device including one or more hardware and software elements, executing software, instructions, programs, and applications, converting and processing signals and information, and performing other related tasks. The processor may be a single chip or integrated with other computing or communications elements.

The memory of the management logic 202 is a hardware element, device, or recording media configured to store data for subsequent retrieval or access at a later time. The memory may be static or dynamic memory. The memory may include a hard disk, random access memory, cache, removable media drive, mass storage, or configuration suitable as storage for data, instructions, and information. In one embodiment, the memory and processor may be integrated. The memory may use any type of volatile or non-volatile storage techniques and mediums.

The management logic 202 may be configured to operate with user input, approval, and instructions or autonomously or semi-autonomously in multiple instances and with multiple display outputs (i.e., screens, views, windows, etc.). For example, the management logic 202 may require user interactions to connect the electronic devices 230-236, perform each test, review the results, save the results, and approve the results as satisfactory.

The interface 204 is an input/output system for interacting with the user audibly, visually, and/or tactilely. The interface 204 may include a keyboard, monitor, mouse, voice control system, touch screen, track ball, or other systems or devices for interacting with a user. In one embodiment, the graphical user interface 206 provides a visual interface for interacting with the user. One embodiment of the graphical user interface 206 is illustrated in FIG. 4. The graphical user interface 206 may display information regarding the connected electronic devices 230-236, device identification and information, user instructions, start-up verification, cosmetic inspection, ongoing CPI removal, software detection, functionality verification, reports, updates, and other information.

The network 226 is a network operable to communicate data, packets, voice signals, and other electronic communications. The network 226 may represent any number of public or private wireline or wireless networks. In one embodiment, the network 226 is an Ethernet network. In another embodiment, the network 226 is a Wi-Fi network that communicates with the testing device 201 through a wireless transceiver. In addition, in certain embodiments, the network 226 may use other wireless technology including, but not limited to, Bluetooth or a proprietary wireless protocol. The network 226 may be utilized to communicate with developer website 228, OEMs, service providers, and other parties to communicate CPI removal reports, problems, libraries, scripts, memory maps, and other electronic communications or resources utilized by the testing device 201.

The libraries 208 includes the electronic information, user instructions, commands, examples, pictures, videos, graphics, models, data, scripts, logic, processor, and programs for performing testing on the electronic devices 230-236. The libraries 208 may include open source or proprietary information and databases. The libraries 208 may store information for any number of device, models and configurations. Non-limiting examples of libraries for Nokia 210, Samsung 212, Motorola 214, Apple 216, and E-devices 218 are shown. The disclosed embodiments may include libraries for any other manufacturer's device. For example, the libraries 208 may provide instructions and corresponding pictures and video for identifying a device and troubleshooting a problem based on user feedback or questions. In one embodiment, textual, audio, and video instructions may be shown simultaneously on the graphical user interface 206. As a result, the user may more effectively process the electronic devices 230-236.

In one embodiment, the libraries 208 may include operator instructions for performing the various types of testing and verification. The libraries 208 may include specific and detailed information for distinct makes and models and additional information for troubleshooting. Additionally, in certain embodiments, the libraries 208 may also include software version and baseband version if applicable to the particular make and model. For example, the libraries 208 may include information designating a baseline memory map and locations in memories of various makes and models that need to be overwritten, searched, or deleted to completely remove the CPI, test functionality, restore default content software and settings, and/or update software. The various manufacturers, service providers or others may provide scripts, programs, or modules configured to perform testing. Likewise, the libraries 208 may store updated user instructions, cosmetic inspection pictures, golden images and screen shots for data and comparison, sequential start up steps and information, updated firmware, operating systems, applications, and other software versions that are installed on the electronic devices 230-236 before, during, or after the testing process.

In one embodiment, the libraries 208 may provide detailed information for working around safety protocols and lock outs of the electronic devices 230-236. The libraries 208 may include screen shots and may allow testing routines to be recorded or generated from the testing device 201.

In another embodiment, the libraries 208 may include applications that are temporarily installed on the electronic devices 230-236 in order to perform testing. For example, for electronic device 234, a Java application may be required to be temporarily installed to interface with the phone. Temporary applications may be required when there is a limited API or the applicable electronic device grants limited privileges to outside systems or devices. The temporary application may perform the testing. Once the temporary application within the libraries 208 has ensured that the testing, such as CPI removal is performed, the temporary application may be deleted or otherwise uninstalled by the testing device 201 or by the applicable electronic device. The testing device 201 may also verify that the temporary application has been removed.

In one embodiment, content within the libraries 208 may include the interface commands and scripts 220, the directory structure 222, and the baseline memory map 224. The commands and scripts 220 provide data, commands, and information, such as how to perform a query, enabling the testing device 201 to interface with specified electronic devices. For example, the directory structure 222 provides details regarding the likely or possible locations of CPI within specified electronic devices. The baseline memory map 224 may provide a template of what a baseline, cleaned, or default memory map, start-up screens, display windows, cosmetic images (e.g. front, back, sides, etc.) installed applications, of an electronic device should be (or be configured) for comparison with an actual or real-time memory map, start-up screen(s), home screens, application list, display windows, and images or visualization of a tested electronic device to perform testing based on specified requirements, criteria, policies, or practices.

The baseline memory map 224 may also identify the types of memory utilized by the electronic device, such as flash memory and a hard drive. In one embodiment, the baseline memory map 224 may also store a scan or electronic imaging of the electronic device 234 before testing for comparison with another baseline memory map 224 or imaging of the electronic device performed after testing. The electronic image or other form of memory map of the electronic devices 230-236 may be stored in the testing device 201 for access by the remote device 231 or other devices, systems or parties. For example, a retailer may access the electronic imaging performed for the electronic device 234 to ensure that testing was performed correctly when servicing or updating the electronic device 234 or addressing a customer issue.

The testing device 201 may include any number of ports, jacks, interfaces, hubs, or electronic interfaces (with or without built-in cords) for physically or wirelessly connecting the electronic devices 230-236 to the testing device 201. In one embodiment, the user may utilize a scanner, keyboard, or other peripheral to manually enter or automatically scan an identifier. The user may then initiate the testing process by making a selection.

In another embodiment, testing may be initiated automatically by the management logic 202 in response to connecting the electronic device 234 to the testing device 201. The testing device 201 automatically determines the identification of the electronic device 234 including identifier (IMEI, serial number, MAC address, etc.), manufacturer, model, variant, and software version for the electronic devices 230-236. The testing device 201 may locate and determines relevant information, such as start-up and home screens, data, pictures, contacts, menu items, called log entries, user applications, and so forth that do not conform to a desired state for the electronic device 234. The desired state may be referred to as the baseline memory map 224 or baseline profile model. In one embodiment, if the testing device 201 does not recognize the electronic device 232, the graphical user may prompt the user to perform identification.

Graphical user interface 206 may prompt the user to enter a model for the electronic device 232. If no model exists, the testing device 201 may prompt the user to enter information or retrieve information for determining the desired state and for configuring the testing device 201 to test the electronic device 232 (or similar devices) for future testing. For example, the user may be prompted to enter a time/date, serial number, identifiers, and state of the device when tested.

The electronic devices 230-236 represent the devices under test. The electronic devices 230-236 may represent any number of electronic devices or appliances (e.g. wireless, wired, standalone, network, etc.). Any combination of the electronic devices 230-236 may be tested simultaneously or concurrently. For example, eight netbook models with a single configuration may be tested simultaneously by the testing device 201. In another example, a test for the electronic device 230 may be initiated and may continue to run while tests are initiated and executed for electronic devices 232 and 334 allowing each of the tests to be implemented separately and run at the same time. In one embodiment, the testing device 201 may include multiple partitions that are accessible to store and test distinct device types and configurations that may have hardware or software conflicts.

Each of the electronic devices 230-236 may require different testing. Testing may involve comparing a desired state (such as a model with a desired configuration for settings, installed software, setup information, CPI removal, and so forth) with a state determined for a model of an electronic device under test and variations and baseline characteristics of that electronic device.

In another embodiment, the testing system 200 may include a remote device 231 locally or remotely executing a desktop application 233. The remote device 231 may be operated by one or more remote users to perform the functions and operations of the testing device 201. In one embodiment, the testing device 201 is a networked device that includes or manages a database including the libraries 208. The testing device 201 may be accessible by the remote device to perform testing of devices that are connected to the remote device 231. The desktop application 233 may include the desktop application 233 for performing the testing herein described. The desktop application 233 may be locally stored and installed, a web interface, or a network application that may be accessible through a server, advanced intelligent network device, or the testing device 201.

In one embodiment, the remote device 231 may be provided to a communications service provider dealer network, retail stores, or other parties that may need to perform testing. For example, the operator of the remote device 231 may have a license and operation agreement with the operator of the testing device 201 to remotely access the testing device 201 or to perform the features and functionality of the testing device 201 including potentially proprietary testing applications, libraries, and processes utilized by the management logic 202 and the libraries 208.

In one embodiment, the remote device 231 may access the databases and functions of the testing device 201 utilizing a SSL connection through the network 226. Other forms of secure communications, channels, or network known to those skilled in the art may alternatively be utilized. The remote device 231 may access information including audit and reporting records for specified devices to determine whether testing has been previously been performed or attempted. As a result, problems, variations, or exceptions may be detected, analyzed, quantified, and documented. The remote device 231 may be granted full access or access on a transaction-by-transaction basis. For example, an operator of the remote device 231 may be required to enter an IMEI that authorizes the remote device 231 to communicate with the testing device 201. The remote device 231 may be utilized to determine whether a device is authorized and cleared for redistribution or whether the device has been compromised.

In one embodiment, the operator of the testing device 201 may charge retailers, refurbishers, and other parties a fee to lease, acquire, or access the functionality of the testing device 201, the desktop application 233, the libraries 208 or services available. For example, the retailer may lease the testing device 201 or the remote device 231 as well as paying for service fees or update costs associated with updates to the desktop application 233 and/or the libraries 208. In another embodiment, the remote device 231 may represent an electronic device that utilizes a desktop application 233, such as a web browser or add-on permanently or temporarily installed, to perform the testing herein described. For example, the desktop application 233 may allow a user to interact with the testing device 201 based on feedback from a technical support person communicating with the user through the graphical user interface 206 of the testing device.

The processes of the illustrative embodiments may be stored as a set of rules or policies that are electronically and/or manually implemented to govern processing of electronic devices. In one embodiment, the rules may be utilized by a processing system, such as a warehouse management system, to ensure that electronic devices found to not conform to applicable standards are properly quarantined until fully tested and verified. Verification indicates that the electronic device has been tested, scanned, and analyzed to confirm that applicable standards are met and no improper CPI or other software or information is included on the electronic device. In one embodiment, the verification may be performed by comparing a memory map before and after (or with a baseline memory map) to ensure testing was performed. Processing of the electronic devices may be performed utilizing bar codes or other machine readable information integrated with, attached to, or associated with each of the electronic devices 230-236.

Figure 3:
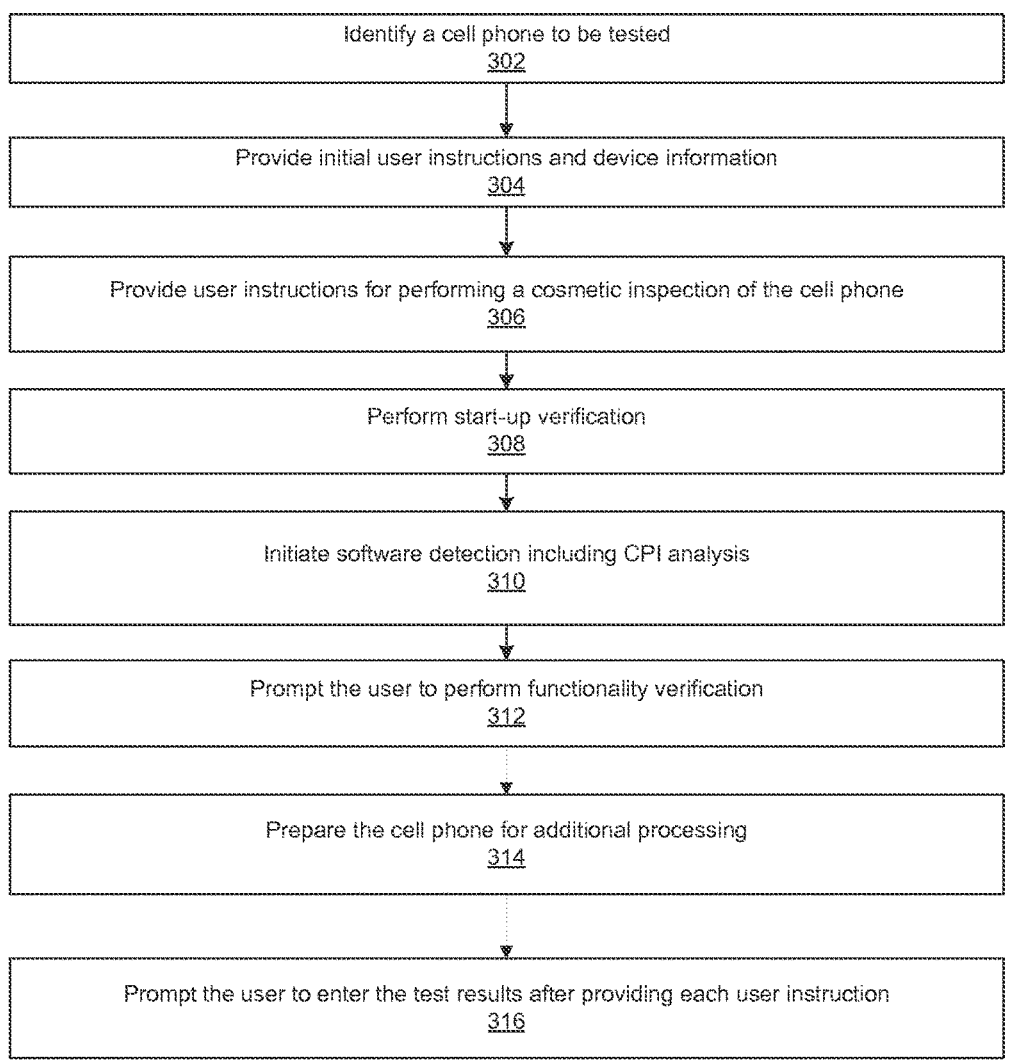
FIG. 3 is a flowchart of a process for processing electronic devices in accordance with an illustrative embodiment.

FIG. 3 is a flowchart of a process for processing electronic devices in accordance with an illustrative embodiment. In one embodiment, the process may be implemented by a testing system as is herein described. The testing system may include one or more robotic arms or input devices, an imaging system, a scanner, a computing device or controller (e.g. processor, memory, logic, programs or applications, graphical user interface, databases, communications interface, keyboards, mouse, microphone for voice commands, etc.), displays, or other similar components. One or more users or operators may interact with the testing system to perform various steps, tests, inspections, and analysis of the selected electronic devices. For purposes of this example, the electronic devices may be referred to as wireless devices, such as cell phones. In one embodiment, the testing system may present a graphical user interface on a computing, communications, or other electronic device to walk the user through the processing steps in a way that is systematic, efficient, and validated.

In another embodiment, the testing system may automatically perform the process of FIG. 3. For example, one or more robotic arms, fingers, plungers, or other selection components may interact with electronic devices to automatically perform the described process.

The process may begin by identifying a cell phone to be tested (step 302). In one embodiment, the cell phone may be identified by the user. For example, the testing system may present information utilizing the graphical user interface of various makes and models of cell phones with an associated picture. The makes and models may be available utilizing an interactive menu, drop-down lists, or so forth for presenting the relevant information. In another embodiment, the testing system may be configured to utilize an imaging system or scanner to identify the cell phone utilizing identifiers, such as serial numbers, bar codes, captured images, wireless signals, or other identifying information.

Next, the testing system provides initial user instructions and device information (step 304). In one embodiment, the user may be displayed device information, such as previous steps, processes, replacements, issues, or notes that are associated with the selected electronic device. The device information may also include a detailed processing history, specifying the user working on the electronic device, the date, the actions performed, and any indicated issues or notes.

In one embodiment, the user instructions may instruct the user to verify an IMEI on a master carton in which the electronic device was shipped with a phone label to verify that they match. The user may also be instructed to wear gloves for all testing, have a clean memory card available, insert the memory card correctly, and insert a known good battery. For example, it may be important to have a functional memory card and battery to perform proper testing and obtain reliable results.

The user instructions may also provide information regarding unlawful images and processing electronic devices, such as "If in the course of working on phones/devices, an image is discovered depicting a person under the age of 18 engaged in sexual conduct, or any other image is found that appears to depict illegal activity, teammates shall escalate to department management who will then contact LP who will collect evidence and submit to law enforcement as needed."

Next, the testing system instructs the user to perform cosmetic inspection of the cell phone (step 306). The testing system or user may verify all areas and sides of the phone a compliant with cosmetic inspection criteria or standards. In one embodiment, the cosmetic inspection criteria may be provided by a communications service provider, OEM, logistics provider, organization, company, or other party. The criteria may be displayed to the user utilizing the testing system or may be available in a physical hard copy referenced by the user. The user may also be instructed to check for non-conforming gaps on all sides of the cell phone. In one embodiment, a touch screen integrated or communicating with the testing system may be utilized to denote issues, damages, scuffs, scratches, cracks, or so forth.

In one embodiment, the testing system may provide user instructions to perform front verification of the cell phone including the main display, protective films and coverings, and ensuring that the front surface conforms to the cosmetic criteria. Next, the testing system instructs the user to perform top and bottom verification. For example, the user may be instructed to verify the headset jack and port(s) are free of damage, rust, and corrosion. Next, the testing system instructs the user to perform side verification. For example, the user may be instructed to verify the volume key, power button, or other buttons or interface components bounce or move freely and are not stiff or sticky. Next, the testing system instructs the user to perform verification for the back of the cell phone. The cell phone may be analyzed with or without a back or battery cover or plate. In one embodiment, the user may be instructed to inspect cell phone components which may include the camera lens and flash, screws (if any), speaker, battery pins, SIM slot, and memory card slot.

Next, the testing system may instruct the user to perform start-up verification (step 308). During step 308 may include power up the phone by holding the power key or button for at least three seconds, verifying startup graphics (without errors). The user may also be prompted to walk through the start-up process for email accounts, required steps, date and type, entering information (e.g. text typing, T9 trace, voice commands, etc.), services, or so forth.

Next, the testing system may initiate software detection including CPI analysis (step 310). The software and CPI detection and analysis may be performed automatically or in response to user input to begin the process. The CPI analysis and removal may be performed as described by application Ser. No. 12/940,331 entitled SYSTEM AND METHOD FOR REMOVING CUSTOMER PERSONAL INFORMATION FROM AN ELECTRONIC DEVICE which is hereby incorporated by reference. The cell phone may be connected to the testing system utilizing a wired connection or wireless connection. In one embodiment, the user may be walked through steps for performing CPI testing including various instructions, windows, slides, or information. For example, the user may be instructed to review various screens or selections presented on the cell phone. The testing system may indicate whether the cell phone passes or fails the CPI tool verification. The testing system may display information for the user to determine whether the test results match the information. In one embodiment steps 310 and 312 may be combined into a number of steps performed by the user.

During step 310, the user may also be prompted to select a calendar, directory, and photo icons or other default or installed applications and verify that the calendar does not include any CPI and is functional before returning to the main menu. The user may also be prompted to verify that there are no downloads listed or displayed. The user may also be prompted to visit music players to verify only approved music including playlists, albums, artists, songs, podcasts, or so forth. The user may be asked to navigate multiple tabs. The user may similarly verify that there is no text, chat, email, images, video, or other messages present on the cell phone.

Next, the testing system prompts the user to perform functionality verifications (step 312). In one embodiment, functionality verification may include placing the cell phone in a sleep mode (e.g. pushing the power button to put the device to sleep), waking the device, and unlocking the device. Between each of a number of functional tests, the user may be prompted to return to a home screen. The user may be prompted to select any number of icons, buttons, or selection components for testing functionality. The user may also verify displayed content (e.g. screen images or display content). The testing system may display default or golden images that provide the standard utilized for performing the comparison. The user may also be prompted to adjust the volume keys to verify minimum or maximum levels or thresholds and verify the vibration functionality. The instructions may guide the user to test search functionality of the cell phone.

During step 312, the user may also be prompted to test a menu key (e.g. button, soft button, programmable buttons, etc.). The user may be walked through main menu screens, setting screens, return screens, and so forth. During navigation of portions of the operating system, applications, and functionality the user may be prompted to verify that there are no phone logs or unauthorized contacts (e.g. contacts to a communications service provider billing department, customer, care, director assistance, data usage, phone usage, and voicemail should be included). The user may also be prompted to verify browser and Internet functionality. For example, the user may verify that default bookmarks are included while other bookmarks have been removed, the browser history is empty, and that there are no saved pages.

During step 312, the user may be instructed to activate one or more integrated cameras (e.g. front facing and rear facing still and video cameras), verify vertical and horizontal viewing, perform a color test by visualizing and taking a picture and/or video of a test screen, verifying the clarity, colors, (and audio for video) and crispness of the captured image and video. For example, the testing system may present a test color wheel for the user to focus on. The user may also delete the image/video and verify that there are not any included images, galleries, or videos in the saved images. The same testing may be performed for a voice recorder and microphone. Audio may be recorded and played back to ensure clarity before being deleted and ensuring that all other video files have been deleted.

The user may also be prompted to ensure that a number of standard or default applications are loaded onto the cell phone. For example, the user may be prompted to slide between displayed screens to verify all of the applications are present. The user may also be prompted to verify the software versions (e.g. operating system, applications, etc.) or so forth. The user may also verify that the IMEI matches information such as a phone identification available through a web browser, database, server, or other data access point. The user may also verify that the IMEI matches the label on the back of the cell phone or device box.

During step 312, the user may be prompted to verify that a default number of ringtones are included, that the speakers plays the ringtones without skipping or static, and that the correct number of ringtones are included (e.g. extraneous or inappropriate ringtones may be deleted). The user may also verify that there are no accounts listed for the cell phone and that the only option is to add an account. The testing system may also prompt the user to verify the applicable memory and memory cards. For example, the user may view the total space and the available space to ensure that data is available. The user may verify that the amounts of space are appropriate.

Next, the testing system may prompt the user to prepare the cell phone for additional processing (step 314). In one embodiment, the user may be prompted to power off the device and remove the batteries and memory cards utilized for testing purposes. In some embodiments, the user may also be prompted to reset the device and restore factor defaults to specific functions or applications.

The testing system may prompt the user to enter the test results after providing each user instruction (step 316). In one embodiment, the results are entered by the user after each user instruction. The results may include a pass or fail indication received by the system. For example, the user may indicate whether the cell phone has passed or failed each step of the cosmetic inspection process, start of verification, software detection and CPI analysis, functionality tests, and so forth. In one embodiment, during step 316 the test results are compiled to be saved independently or grouped with other test results that are saved locally or remotely.

The test results may be entered into the testing system during the actual testing or after the fact. The test results may be entered for individual devices, multiple devices, or batches of devices. The testing system may be configured to allow the user to test a number of electronic devices simultaneously, concurrently, or sequentially. The test results may be saved to the testing system for review by any number of auditors, administrators, quality control inspectors, secondary reviewers or operators, communications service providers, manufacturers, or other relevant parties. The test results may be compiled to generate reports indicating the results of each testing step to determine where the process of FIG. 3 or other relevant processes are failing.

FIG. 4 is a pictorial representation of a graphical user interface 400 for testing an electronic device in accordance with an illustrative embodiment. The graphical user interface 400 is one embodiment of an interface that may be presented. The graphical user interface 400 may include information that is automatically populated based on the applicable testing process. Additionally, the graphical user interface 400 may allow interaction with any number of libraries or databases. For example, the graphical user interface may be specifically populated based on one or more makes and models of electronic devices selected for testing.

In one embodiment, the user may be required to present identification information, such as a username, password, company identification, or other access information to access the graphical user interface 400 and/or control the testing device in person or remotely.

In one embodiment, the graphical user interface 400 may indicate whether the testing has been initiated. In addition, the graphical user interface 400 may indicate whether the device is functional, software and operating systems are up-to-date, and whether CPI has been verifiably removed or is still present. The graphical user interface 400 may also indicate the electronic device identifier, file locations(s) of CPI or other files, file types, a party the electronic device is received from, date the CPI was cleared, a user in charge of removing the CPI, and the CPI removal reports sent and received.

The graphical user interface 400 may include any number of views, tabs, icons, toggle buttons, indicators, graphical components, windows, and access information for initiating, managing, and reviewing the CPI detection and removal from electronic devices. For example, the graphical user interface 400 may be utilized to generate reports or audits for specific electronic devices or for groups of electronic devices (such as lots or batches of electronic devices received).

The graphical user interface 400 may include any number of fields and menus for selecting the electronic devices for testing. The graphical user interface 400 may also present options, look-up features, and input fields for adding new device types (i.e., new makes and models) for updating the logic and libraries utilized to perform testing. The graphical user interface 400 may allow a user to indicate whether start-up was initiated and verified, functionality is verified, the operating system and other software is up-to-date or restored, co-branding is properly installed, updated, or removed, settings are properly configured, memories are cleared or verified, and any issues. The user may be prompted to enter in any custom or auto populated selections for keeping records and tracking issues for inventory management and reporting to any number of manufacturers, service providers, and others. For example, a particular defect may be cited for specific devices for reconfiguring or fixing specific devices.

Figure 5:
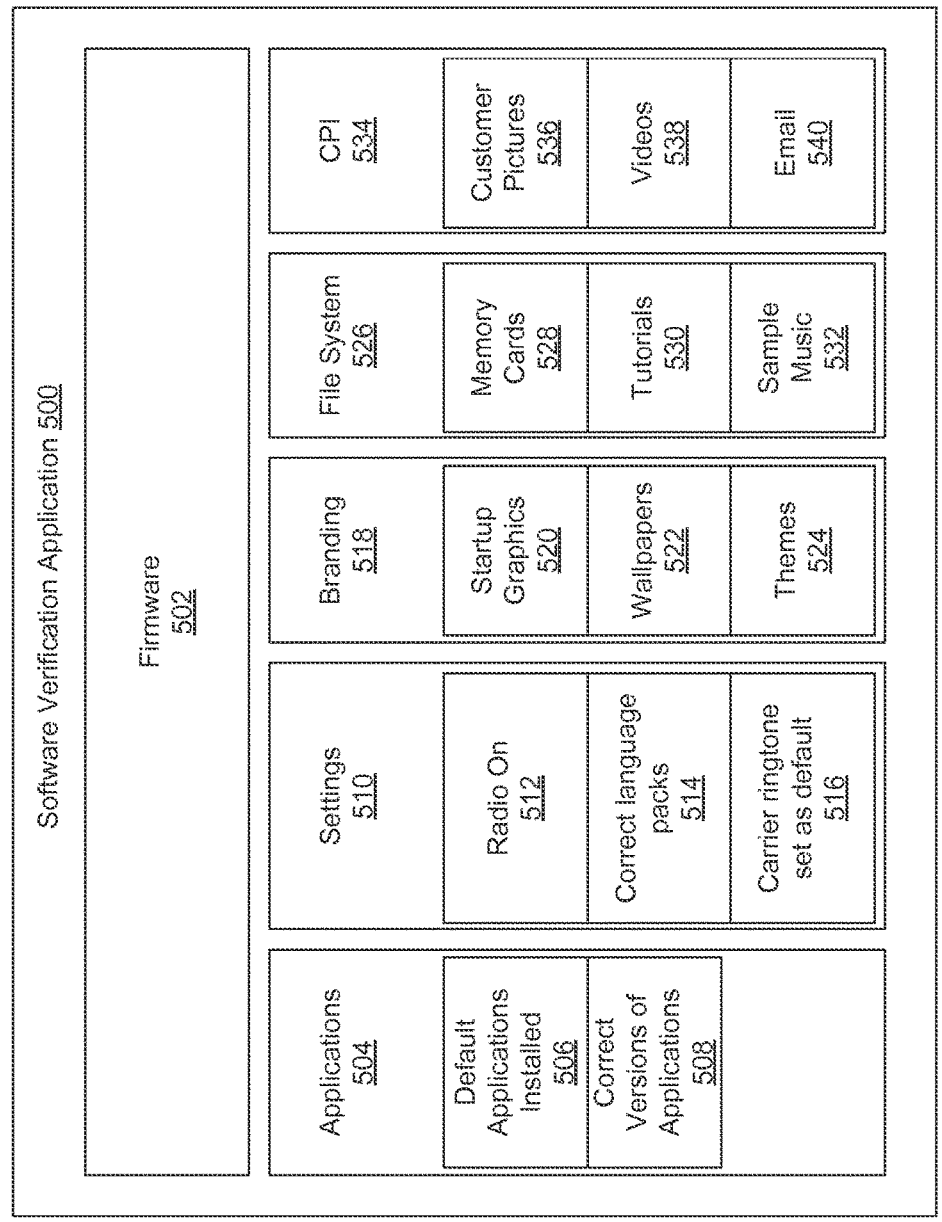
FIG. 5 is a pictorial representation of a testing application in accordance with an illustrative embodiment.

FIG. 5 is a pictorial representation of a testing application 500 in accordance with an illustrative embodiment. The testing application 500 may be executed and utilized by any of the previously described devices. In addition, the testing application 500 may be bundled with any of the other programs, applications, or instructions herein disclosed.

The testing application 500 may be executed by a computing device (i.e. including a process, memory, database, etc.), such as a server or electronic device utilizing a processing unit. The computing device may include an interface for communicating with one or more electronic devices, such as mobile phones sequentially, simultaneously, or concurrently. For example, the interfaces may include USB ports and wired connections or connectors, wireless transceivers (i.e. Wi-Fi, Bluetooth), or other communications mediums for connecting the one or more electronic devices to the computing device. Tests on multiple devices may be implemented simultaneously, concurrently, sequentially, or in parallel.

In one embodiment, the testing application verifies the electronic resources of the tested units or devices. For example, the firmware 502 represents the firmware and software utilized by an electronic device. The firmware and software may include operating systems, applications, settings, configurations, branding, marketing, and advertising content, and other software.

The testing application 500 may be utilized to verify the firmware 502, applications 504, settings 510, branding 518, file system 526, and CPI 534. In addition, the testing application 500 may verify default content (not shown) for an electronic device that may not be otherwise categorized. The applications 504 may include default applications installed 506, correct versions of applications, user preferences, or application usage information. The settings 510 may include radio settings 512, correct language packs 514, and carrier ringtone set as default. The branding 518 may include startup graphics, wallpapers 522, and themes 524. The file system may include memory cards 528, tutorials, 530, and sample music 532. For example, the sample music 532 is indicative of any sample files, such as music, pictures, videos, or so forth. The CPI may include customer pictures 536, videos 538, and email 540. The email 540 may be indicative of any electronic message, such as chat messages, tweets, texts, picture messages, video messages, emails, audio messages, or so forth. The testing application 500 may also verify and clear any number of file systems, memories, caches, databases or other components that vary from the referenced unit.

The previous detailed description is of a small number of embodiments for implementing the invention and is not intended to be limiting in scope. The following claims set forth a number of the embodiments of the invention disclosed with greater particularity.

What is claimed:

1. A method for processing an electronic device, the method comprising:
   identifying the electronic device;
   retrieving user instructions associated with the electronic device utilizing a testing system;
   communicating from the testing system the user instructions for performing cosmetic inspection of the electronic device, customer personal information (CPI) analysis of select installed applications of the electronic device, software analysis of the electronic device, and functional testing, wherein the CPI analysis of the electronic device comprises identifying CPI on the electronic device and verifiably removing the CPI from the electronic device in response to detecting the CPI on the electronic device by evaluating a before and after memory map;
   temporarily quarantining the electronic device until verification is received of implementation of the user instructions;
   receiving verification information from a user of implementation of the user instructions;
   clearing memory, by the testing system, in response to CPI not verifiably removed.

2. The method according to claim 1, further comprising physically or wirelessly connecting the electronic device to the testing system.

3. The method according to claim 1, wherein the identifying is performed utilizing a scanner of the testing system.

4. The method according to claim 1, wherein the user instructions are stored in a database of the testing system, and wherein the user instructions are associated with the make and model of the electronic device.

5. The method according to claim 1, wherein the user instructions are communicated to one or more displays in communication with the testing system.

6. The method according to claim 1, wherein software analysis includes restoring a default software and settings of the electronic device.

7. The method according to claim 1, wherein the functional verification includes at least start up testing, camera testing, and user interface testing.

8. The method according to claim 1, further comprising:
   generating test results for the electronic device in response to the verification information; and
   saving the test results associated with the electronic device.

9. The method according to claim 1, further comprising generating a report for a plurality of electronic devices compiled from a plurality of electronic devices.

10. A testing system comprising:
    a processor for executing a set of instructions; and
    a memory for storing the set of instructions, wherein the set of instructions are executed to:
    identify an electronic device;
    retrieve user instructions associated with the electronic device utilizing a testing system;
    present the user instructions for performing cosmetic inspection of the electronic device, customer personal information (CPI) analysis of select installed applications of the electronic device, software analysis of the electronic device, and functional verification, wherein the CPI analysis of the electronic device comprises identifying CPI on the electronic device and verifiably removing the CPI from the electronic device in response to detecting the CPI on the electronic device by evaluating a before and after memory map;
    temporarily quarantine the electronic device until verification is received of implementation of the user instructions; and
    receive verification information from a user of one or more of the user instructions;
    clear memory, by the testing system, in response to CPI not verifiably removed.

11. The testing system according to claim 10, wherein the identifying is performed utilizing a scanner of the testing system.

12. The testing system according to claim 10, wherein the user instructions are stored in a database of the testing system, and wherein the user instructions are associated with the make and model of the electronic device.

13. The testing system according to claim 10, wherein software analysis includes updating software and settings of the electronic device.

* * * * *